United States Patent [19]
Ren et al.

[11] Patent Number: 6,027,508
[45] Date of Patent: *Feb. 22, 2000

[54] STENT RETRIEVAL DEVICE

[75] Inventors: Brooke Q. Ren, Champlin; Roger N. Hastings, Maple Grove, both of Minn.

[73] Assignee: SciMed Life Systems, Inc., Maple Grove, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/735,303

[22] Filed: Oct. 3, 1996

[51] Int. Cl.⁷ ..................................................... A61F 11/00
[52] U.S. Cl. ............................................... 606/108; 606/1
[58] Field of Search ........................ 606/1, 108, 191–200

[56] References Cited

U.S. PATENT DOCUMENTS

| | | |
|---|---|---|
| 3,421,509 | 1/1969 | Fiore . |
| 3,657,744 | 4/1972 | Ersek . |
| 3,842,441 | 10/1974 | Kaiser . |
| 3,993,078 | 11/1976 | Bergentz et al. . |
| 4,130,904 | 12/1978 | Whalen . |
| 4,140,126 | 2/1979 | Choudhury . |
| 4,313,231 | 2/1982 | Koyamada . |
| 4,315,509 | 2/1982 | Smit . |
| 4,434,797 | 3/1984 | Silander . |
| 4,483,339 | 11/1984 | Gillis . |
| 4,512,338 | 4/1985 | Balko et al. . |
| 4,562,596 | 1/1986 | Kornberg . |
| 4,594,996 | 6/1986 | Ibrahim et al. . |
| 4,732,152 | 3/1988 | Wallsten et al. . |
| 4,733,665 | 3/1988 | Palmaz . |
| 4,739,762 | 4/1988 | Palmaz . |
| 4,744,366 | 5/1988 | Jang . |
| 4,776,337 | 10/1988 | Palmaz . |
| 4,793,348 | 12/1988 | Palmaz . |
| 4,800,882 | 1/1989 | Gianturco . |
| 4,886,062 | 12/1989 | Wiktor . |
| 4,907,336 | 3/1990 | Gianturco . |
| 4,913,141 | 4/1990 | Hillstead .................................. 606/108 |
| 4,921,478 | 5/1990 | Solano et al. .............................. 604/53 |
| 4,932,959 | 6/1990 | Horzewski et al. ..................... 606/194 |
| 5,026,377 | 6/1991 | Burton et al. ............................ 606/108 |
| 5,053,013 | 10/1991 | Ensiminger et al. ................... 604/167 |
| 5,156,596 | 10/1992 | Balbierz et al. ......................... 604/164 |
| 5,275,605 | 1/1994 | Winkler .................................... 606/128 |
| 5,330,482 | 7/1994 | Gibbs et al. .............................. 606/113 |
| 5,334,208 | 8/1994 | Soehendra et al. ...................... 606/108 |
| 5,388,590 | 2/1995 | Horrigan et al. . |
| 5,409,495 | 4/1995 | Osborn ..................................... 606/108 |
| 5,411,507 | 5/1995 | Heckele ................................... 606/108 |
| 5,464,408 | 11/1995 | Duc ........................................... 606/108 |
| 5,474,563 | 12/1995 | Myler et al. ............................. 606/108 |
| 5,520,697 | 5/1996 | Lindenberg et al. .................... 606/108 |
| 5,593,394 | 1/1997 | Kanesaka et al. ....................... 604/282 |

FOREIGN PATENT DOCUMENTS

| | | |
|---|---|---|
| 0 274 846 A1 | 7/1988 | European Pat. Off. . |
| 2 104 673 | 3/1972 | Germany . |

*Primary Examiner*—Glenn K. Dawson
*Attorney, Agent, or Firm*—Crompton, Seager & Tufte, LLC

[57] ABSTRACT

A device and method for retrieving partially deployed balloon expandable stents. The device addresses, inter alia, the problem of retrieving stents that have become dislodged from the desired position about a deploying balloon, leaving a stent that is likely too large to be retracted back into a guide catheter. The device can be used with a guide catheter having a balloon angioplasty catheter inserted within. The invention includes a grasping device at the distal end of a shaft and a mechanism for opening and closing the grasping device. In one embodiment, the grasping device includes a reinforced tube having a bound outer inflatable sleeve and a longitudinal slit. In use, the tube can be slipped over the proximal portion of a balloon catheter shaft extending from a patient, advanced over the shaft, through and distally out of a guide catheter, there inflated to grasp the stent distal end, and retracted proximally into the guide catheter. In another embodiment, the grasping device includes fingers attached distally to an inner shaft and proximally to an outer shaft. The fingers open when sliding the inner shaft distally relative to the outer shaft. The fingers close when sliding the inner shaft proximally relative to the outer shaft. This embodiment can be used with a guide catheter to grasp a stent and withdraw it through the guide catheter.

18 Claims, 3 Drawing Sheets

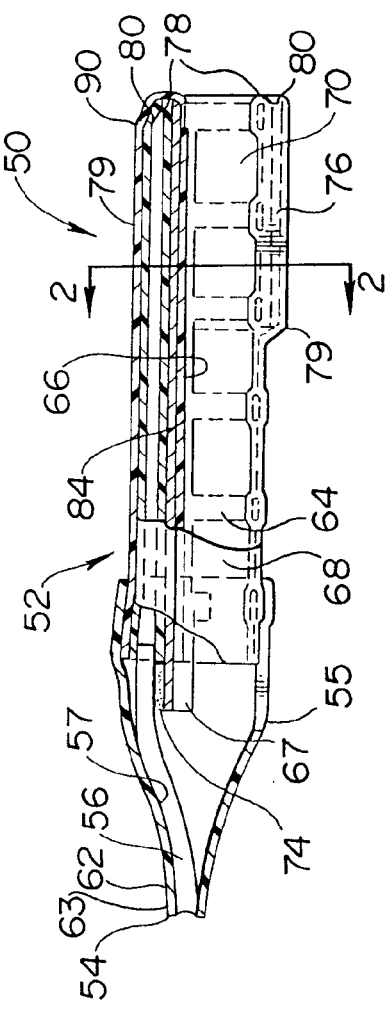
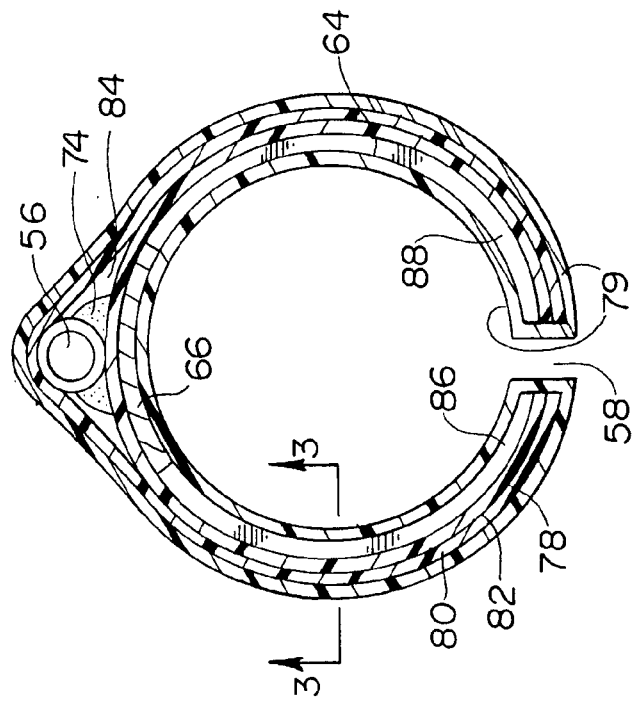
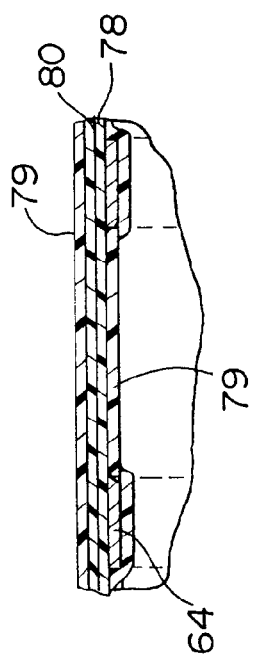

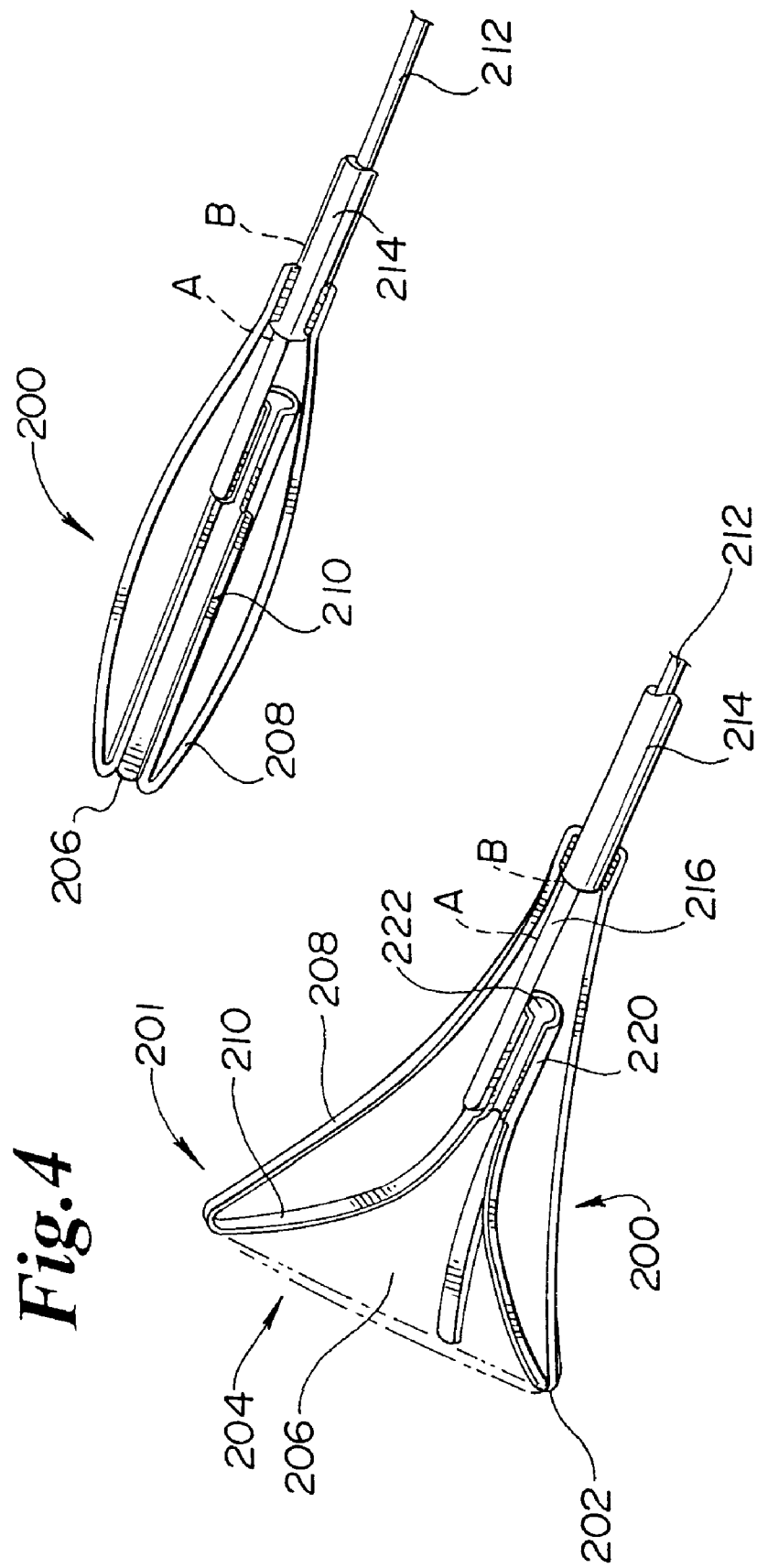

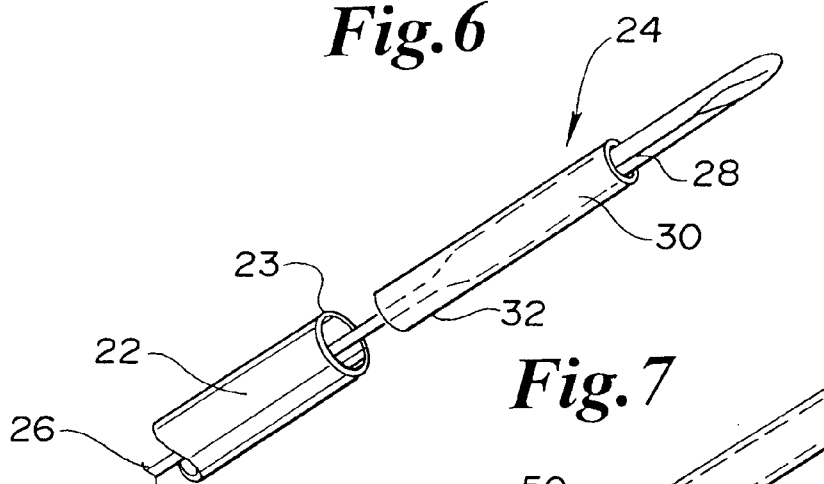
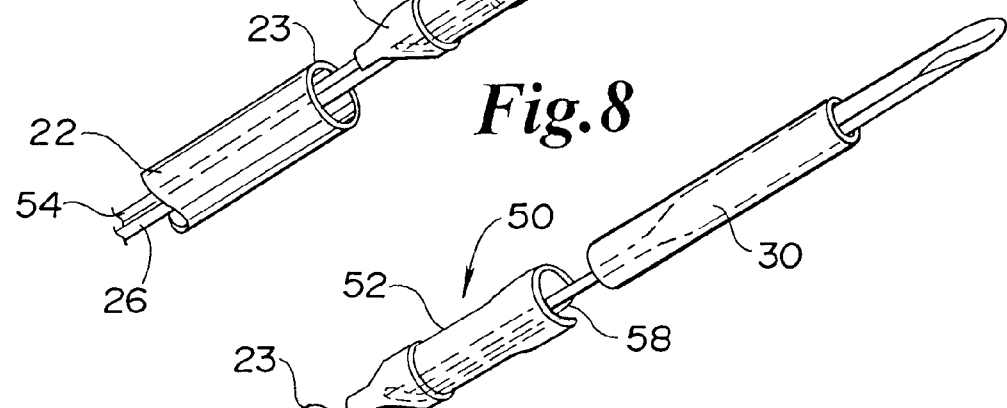
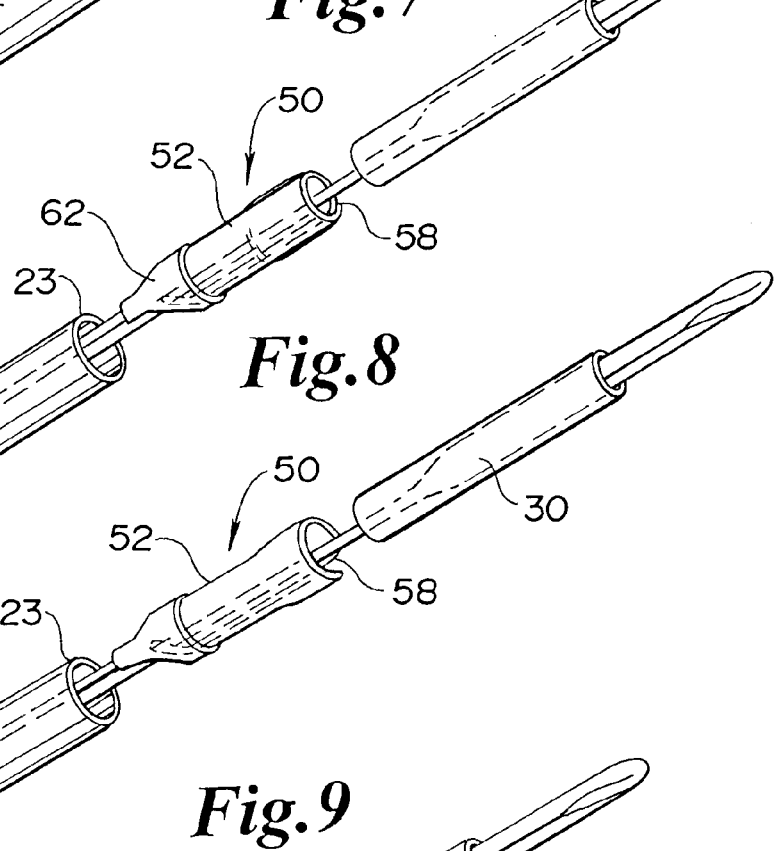
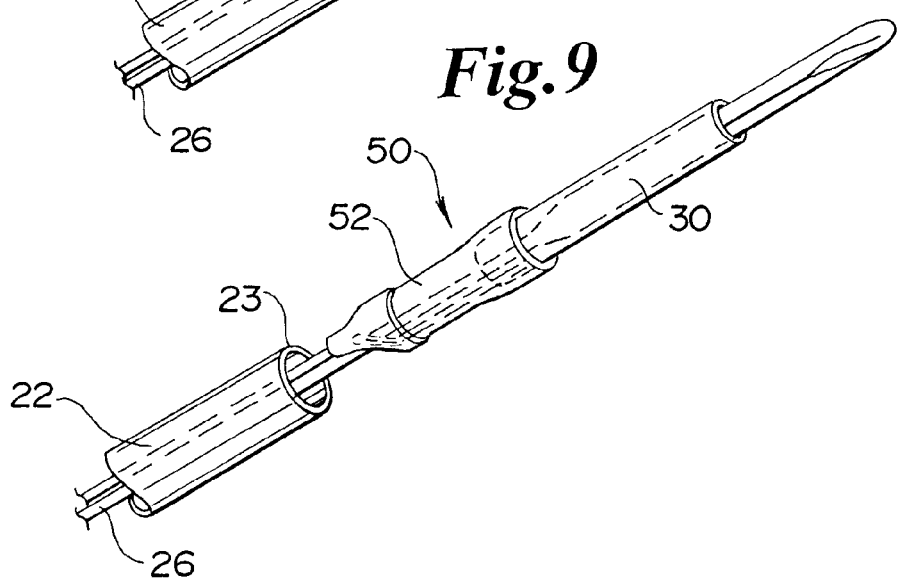

STENT RETRIEVAL DEVICE

FIELD OF INVENTION

The present invention relates generally to a method and device for stent retrieval. In particular, the invention relates to a device for retrieving balloon expandable stents what are less than fully deployed.

BACKGROUND OF THE INVENTION

Stents are increasingly used in Percutaneous Transluminal Coronary Angioplasty (PTCA). PTCA is a well established procedure for dilating stenosed vessel regions in the heart. In this procedure, a balloon angioplasty catheter is introduced into the vasculature, typically though an incision in the femoral artery in the groin. The balloon catheter is advanced through the femoral artery, through the aortic arch, and into the artery to be treated. The balloon is advanced across a lesion and inflated, dilating the vessel at the location of the balloon expansion. The dilation increases the vessel cross sectional area and the resultant blood flow.

Over a period of time, the dilated vessel section may narrow again, in part due to a rebound from the angioplasty procedure, thereby reversing some of the benefits of the angioplasty. To prevent this vessel narrowing, stents are increasingly used. Stents are placed across the dilated region and radially expanded, opposing any inward radial force by the vessel walls.

Stents may be categorized as self-expanding and balloon expanding. The self-expanding stents are contained within a sheath to prevent premature expansion. The stent is typically placed on a balloon catheter which is inserted into a guide catheter and moved across a lesion. Once the stent is in position for deployment, the sheath is pulled back and the stent, being biased to expand, expands, ideally with sufficient force to resist the vessel wall rebound force which can occur after angioplasty. The stent can be left in place indefinitely.

Balloon-expandable stent deployment requires "tacking up" the stent, forcing the stent radially outward into contact with the vessel wall. The stent is mounted over an uninflated balloon, crimped, and the balloon with stent advanced within a guide catheter. The balloon with the mounted stent is advanced distally out of the guide catheter across the lesion. The balloon is inflated, expanding the stent, thereby tacking the stent in place. For optimal stent placement, it is necessary for the stent to be properly positioned axially on the balloon prior to balloon inflation. A non-compliant balloon operated at high pressure is typically used to expand the inside diameter of the stent, forcing it against the vessel interior walls. The balloon is deflated, and withdrawn proximally into the guide catheter.

For both types of stents, self-expanding and balloon expandable, a sheath is often used during stent delivery, being interposed between stent and guide catheter. The sheath adds to the profile of the stent, increasing the guide catheter inside diameter required to pass the sheathed stent and decreasing the ability to navigate the delivery system distally. In one case, when using a sheath, a sheath outside diameter of 72 mils (thousands of an inch) is required to place a stent having an outside diameter of 60 mils. When not using a sheath, clearance is only required for the 60 mil sheath. This reduced outer diameter translates into increased vascular accessibility for stent placement, making treatable otherwise untreatable lesions.

As a result of the increased vascular accessibility without sheaths, treating physicians increasingly prefer to place stents without using a sheath, commonly referred to as the "bare mounting" technique. This is possible with balloon-expanding stents, but has associated difficulties. A stent can be bare mounted over a balloon, crimped, and the balloon advanced through the guide catheter to the distal region of the guide catheter, which is positioned proximal to the vessel region having a lesion. The balloon with stent is advanced distally out of the guide catheter and across the lesion. When the stent is crimped onto the balloon, there is often a slight recoil, such that when balloon and stent are advanced out of the guide catheter, the stent is too large to be retracted into the guide catheter even before balloon inflation.

Occasionally, there are situations where the stent becomes partially or totally dislodged from the balloon. The dislodged stent may be detected while still within the guide catheter. A dislodged stent can be detected using radiography, observing relative positions of radiopaque regions on the stent and guide catheter. When the stent is dislodged while within the guide catheter, it may be possible to withdraw the guide catheter, the balloon catheter and stent together.

At other times, the stent becomes dislodged after the stent has been advanced out of the guide catheter. As the balloon-expanding stents do not self-expand, this creates the situation where a stent may become loose in the vasculature. When the stent is only partially dislodged from the balloon, the balloon with partially mounted stent may be withdrawn proximally into the guide catheter. The stent outer diameter is often only slightly less than the inner diameter of the guide catheter. If there is any recoil from crimping, the stent outer diameter may be larger than the guide catheter inner diameter, and withdrawal of the balloon will not withdraw the stent, but may instead force the stent off the balloon.

In cases where the stent remains sufficiently small to fit within the guide catheter, withdrawal may still prove problematic. During attempted recovery, there is a point at which the proximal edge of the stent is to be withdrawn proximally past the distal edge of the guide catheter. If the stent is not centered relative to the longitudinal axis of the guide catheter, the guide catheter distal edge may catch against the stent proximal edge, forcing the stent from the balloon.

What would be desirable is a device for retrieving a partially deployed stent. A device for grasping, compressing, and retracting a stent has not hereto been provided.

SUMMARY OF THE INVENTION

The present invention provides a device and method for retrieving partially deployed balloon expandable stents from within a body conduit such as a vein or artery. While the preferred use of the invention is to retrieve coronary stents, use in retrieving stents from other body conduits is contemplated and is explicitly within the scope of the invention. The invention allows retrieval of stents that are otherwise too large or not aligned to be withdrawn into a guide catheter.

This can be accomplished by side mounting a stent retriever over the proximal end of a balloon catheter shaft, advancing the retriever through the guide catheter to the stent, grasping the stent, and withdrawing it into the guide catheter. While the preferred embodiment mounts over a balloon catheter shaft, the invention may be mounted over other shafts, including guide wires, and may be used without any shaft at all. The preferred embodiment is advanced within a guide catheter, but advancement within other elongate tubes is contemplated and is also within the scope of the invention.

In one embodiment, the retrieval device includes an elongate shaft having a longitudinally slit tube mounted at the distal end. The preferred tube includes a metal (e.g., stainless steel or a super-elastic alloy) spine and rib cage having an inflatable sleeve bonded to the exterior, exclusive of the slit. The shaft preferably includes a hypotube in fluid communication with the inflatable sleeve. The tube interior and exterior are wrapped in laminate, further securing the sleeve to the tube. The transition from tube to shaft includes a shoulder, preferably formed of polymeric material. When inflation fluid is supplied to the inflatable sleeve, the sleeve opens the slit tube, increasing the inside diameter, enabling the capture of a stent.

In use, the slit tube is mounted over a shaft lying within a guide catheter, such as a stent placement balloon shaft. The tube is advanced through the guide catheter to the stent to be captured. Inflation fluid is supplied to inflatable sleeve, opening the rib cage and increasing the tube inside diameter. The tube distal end is advanced over the stent proximal end, and the inflation pressure removed. The tube returns to the smaller inside diameter, capturing and compressing the stent proximal end. The slit tube holding the stent is withdrawn through the guide catheter.

In another embodiment, the retrieval device for use with a guide catheter includes an elongate shaft having a grasping device mounted at the distal end. One preferred embodiment grasping device includes radially distally diverging fingers having an elastomeric web covering. In one embodiment, the grasping device includes fingers attached distally to an inner shaft and proximally to an outer shaft. The fingers open when sliding the inner shaft distally relative to the outer shaft. The fingers close when sliding the inner shaft proximally relative to the outer shaft. Another preferred embodiment includes an attachment hub having a longitudinal cavity for side mounting the device over a shaft.

In use, the grasping device is mounted over a shaft that lies within a guide catheter, compressed to constrain the fingers, inserted through the guide catheter, exiting the guide catheter distally near the stent. In the preferred embodiment, the fingers expand radially when the inner shaft is slid distally from the outer shaft distal end. The grasping device distal end is advanced over the stent proximal end, and closed by sliding the inner shaft proximally relative to the outer shaft. The fingers are closed over the stent, and the grasping device holding the stent is withdrawn through the guide catheter.

BRIEF DESCRIPTION OF THE DRAWINGS

FIG. 1 illustrates a side view of a slit tube grasping device having an inflatable sleeve;

FIG. 2 is a cross sectional view of the device of FIG. 1, taken along 2—2;

FIG. 3 is an enlarged, cross-sectional view of a portion of the tube wall of the embodiment of FIG. 2, taken along 3—3;

FIG. 4 is a perspective view of a grasping device including webbed fingers, shown in open position;

FIG. 5 is a perspective view of the device of FIG. 4, shown in closed position;

FIG. 6 illustrates a perspective view of a partially deployed stent, balloon catheter, and guide catheter;

FIG. 7 further illustrates the perspective view of FIG. 6, including the stent retrieval device of FIG. 1 before stent capture and before inflation;

FIG. 8 further illustrates the perspective view of FIG. 6, including the stent retrieval device of FIG. 1 before stent capture after inflation; and FIG. 9 further illustrates the perspective view of FIG. 6, including the stent retrieval device of FIG. 1 after stent capture.

DETAILED DESCRIPTION OF THE PREFERRED EMBODIMENTS

FIG. 1 illustrates a stent retrieval device 50 embodying the present invention including a tube portion 52 and a shaft portion 54, tube 52 being attached to a distal region 55 of shaft 54, and having a proximal shoulder 62 decreasing in diameter from tube 52 to shaft 54. A preferred embodiment includes a longitudinal slit 58 running the entire length of tube 52 for side mounting tube 52 over a balloon catheter shaft. Tube 52 can be mounted over the proximal region of a balloon catheter shaft extending proximally from a guide catheter within the patient. In a preferred embodiment, tube 52 includes radial reinforcing ribs 64 joined to a longitudinal spine 66, and proximal interstitial regions 68 and distal interstitial regions 70 between ribs 64.

A preferred method of making ribs 64 and spine 66 is to laser cut a piece of NITINOL tubing, for example, 0.063 inch outside diameter tubing having 0.004 inch wall thickness. The laser cutting leaves spine 66 and ribs 64 as a single piece.

Shaft 54 can be fixedly attached near distal region 55 to spine 66 at spine stem 67 by soldering, as indicated at 74. In a preferred embodiment, shaft 54 includes a stainless steel hypotube 57 which includes inflation lumen 56. In one embodiment, hypotube 57 is open only at the extreme distal end, achieving fluid communication with the sleeve, described below.

A preferred embodiment tube 52 has an inflatable sleeve 76 including inner wall 78 and outer wall 80, having sleeve fluid spaces 82 and 84 therebetween. Sleeve 76 substantially covers the outside of tube 52 including ribs 64, spine 66, and interstitial regions 68 and 70, but not covering slit 58. In a preferred embodiment, only the distalmost half of tube 52 is covered by sleeve 76. In a preferred embodiment, sleeve 76 can be formed by bonding an inflatable balloon, such as an angioplasty balloon, over the circumference of tube 52, leaving slit 58 open. A preferred sleeve material is polyamide elastomer. A preferred method of bonding sleeve to ribs and spine utilizes adhesive. Fluid space 82 is in fluid communication with inflation lumen 56 and includes an inflation fluid conduit 84, preferably running longitudinally along spine 66. In a preferred embodiment, a balloon, which can be an angioplasty balloon, is attached to the distal end of hypotube 57, and fluid conduit 84 and fluid space 82 are part of the balloon interior.

The preferred embodiment includes a shoulder cover 63 over shoulder 62, providing a transition from tube 52 to shaft 54. In one embodiment, shoulder 62 is conical shaped. In another preferred embodiment, shoulder 62 has a contour as illustrated in FIG. 1. In a preferred embodiment, shoulder cover 63 is formed from polyolefin. Shoulder cover 63 can be formed by wrapping a piece of polymeric material over shoulder 62 and bonding it in place using adhesive.

Tube 52 and sleeve 76 are further covered by laminate layer 79. Laminate 79 is bonded over sleeve 76 both inside and outside tube 52, serving to further secure sleeve 76 to tube 52. In a preferred embodiment, laminate can be formed from angioplasty balloon material, cutting off both ends, creating a tube of balloon material, tucking a longitudinal strip of material inside tube 52 through slit 58, and leaving the remainder outside tube 52. In the preferred embodiment, the laminate material is polyamide elastomer. Laminate 79 can be secured in place using adhesive.

FIG. 2 illustrates a cross section taken the distal portion of tube 52 between ribs 64. Ribs 64 are shown divided into long rib 86 and short rib 88 by slit 58. In a preferred embodiment, slit 58 is not located directly opposite spine 66. In another preferred embodiment, slit 58 is located 90 degrees relative to spine 66. Sleeve inner wall 78 and outer wall 80 are both exterior to ribs 64. Laminate 79 is shown, covering both inside and outside surfaces of tube 52.

FIG. 3 shows an enlarged cross-sectional view of the wall of tube 52. Proceeding from inside to outside, FIG. 3 shows laminate 79, rib 64, sleeve inner wall 78, sleeve outer wall 80, and laminate 79.

Referring again to FIG. 2, when inflation fluid is provided from inflation fluid conduit 84, fluid is channelled under pressure to sleeve fluid space 82 between inner wall 78 and outer wall 80, forcing the wall material apart. If the sleeve material were freely draped over tube 52, inflation pressure would cause the lower portions of the sleeve to rise, eventually inflating the sleeve to the expected round cross section of a balloon. Sleeve material of the preferred embodiment is adhesively secured to underlying tube 52 and further wrapped in laminate 79, restricting free sleeve movement. Sleeve inner wall 78 and outer wall 80 are also restricted from fully inflating, being wrapped in laminate 79. The force of inflation, in the preferred embodiment being approximately 4 atm, acts to straighten out sleeve 76. The result being that sleeve 76 partially straightens out, forcing ribs 64 apart, increasing the inside diameter of tube 52.

In the preferred embodiment, only the distal portion of tube 52 is surrounded by sleeve 76, and only the distal portion of tube 52 opens up. The resultant opening can be sufficiently large to grasp a partially deployed stent. When inflation pressure is removed, tube 52 ribs 64 attempt to assume the pre-inflation dimensions, which can compress the end of the grasped stent.

With the stent grasped by tube 52, tube and stent can be withdrawn into the guide catheter. Shoulder 62 serves to center tube 52 within a guide catheter, easing the withdrawal into the guide catheter.

FIG. 4 illustrates another embodiment of the invention, shown in open position. Stent retrieval device 200 can include a first, inner shaft 212 having a distal region 216, a second shaft 214, slidable relative to first shaft 212, and a grasping device 201 attached near distal region 216. In the preferred embodiment, grasping device 201 includes a plurality of fingers 202 and a web 206 between fingers 202. In a preferred embodiment, first shaft 212 is attached at a more distal region of fingers 202 than the attachment region of second shaft 214. In a preferred embodiment, fingers 202 are formed of NITINOL. In a preferred embodiment, the web is formed of an elastomeric material, most preferably silicone elastomer.

In a preferred embodiment, there are three fingers, each including an inner member 210 and an outer member 208. The preferred size for the members is 10 mm in length. At the proximal end, inner members 210 are attached to first shaft distal region 216. In one embodiment, inner members 210 are attached directly to first shaft 212. In the preferred embodiment, inner members are operatively attached to first shaft 212 through soldering to an attachment hub 220. In this embodiment, attachment hub 220 includes a longitudinal cavity 222 for receiving an inserted catheter shaft. At the proximal end, outer members 208 are attached to second shaft 214, slidable relative to first shaft 212. In the preferred embodiment, depicted in FIG. 4, second shaft 214 is hollow and contains first shaft 212 therein.

Hub 220 may be formed by bending a metal piece over a circular mandrel, forming cavity 222. A finger having an inner and outer member 210 and 208 may be formed by bending a single piece of NITINOL into the shape illustrated in FIG. 4, with inner member 210 diverging and outer member 208 converging, the fingers radially expanding when open. Second, outer shaft 214, preferably made of polyimide, and may be secured to the proximal end of outer members 208.

FIG. 5 shows the embodiment of FIG. 4 in a closed position. Second shaft 214 is shown in closed position A in FIG. 5 and open position B in FIG. 4. Both inner members 210 and outer member 208 are formed of metal in the preferred embodiment, preferably NITINOL. In one embodiment, inner members 210 have a diverging, bowed shape, and outer members 208 a converging, bowed shape when open, as depicted in FIG. 4. When fingers 202 are forced into a closed configuration, as for insertion into a guide catheter, as shown in FIG. 5, inner members 210 assume a straight shape, and outer members 208 bow opposite to their former curvature.

In use, when a balloon catheter is positioned in the patient within a guide catheter and having a partially deployed stent near the balloon, the distal region of a stent retrieval device is side mounted over a proximal region of the catheter shaft laying outside the patient. The grasping device portion of the retrieval device is advanced into the patient, distally out of the guide catheter, to the stent. The second shaft can be pulled, or the first shaft pushed, to open the grasping device. The grasping device is advanced over the stent, and the first shaft pulled or the second shaft pushed, to close the grasping device. The stent is grasped and pulled back into the guide catheter and withdrawn from the patient.

FIGS. 6–9 illustrate the use of the present invention.

The embodiment of FIG. 1 is used for illustrative purposes, but the illustrations substantially apply to other embodiments as well.

FIG. 6 illustrates a guide catheter 22, including a distal end 23, having an inflatable balloon catheter 28 inserted therethrough, including a catheter shaft 26, and balloon 28. Stent 30 is shown, having slipped proximally from the desired, mid-balloon position. Distal slippage presents a similar problem. Stent 30 includes a proximal end 32 having an outside diameter nominally the same as the inside diameter of guide catheter distal end 23. As shown, withdrawing balloon catheter 24 into guide catheter 22 presents the possibility of guide catheter distal end 23 pushing stent 30 distally off balloon 28. Even in situations where stent 30 has an outer diameter small enough to fit within guide catheter 22, the possibility of guide catheter 22 dislodging stent 30 upon catheter withdrawal remains. This possibility exists if catheter shaft 26 is not sufficiently centered within guide catheter 22, thereby allowing stent 30 to be withdrawn proximally while off-center. Such an off-center withdrawal can allow stent 30 to be pushed distally by part of guide catheter distal end 23.

FIG. 7 illustrates the stent retrieval device embodiment of FIG. 1, distal of guide catheter distal end 23, tube 52 having been side mounted over catheter shaft 26 using slit 58. The device is shown in a pre-inflated, non-pressurized state. FIG. 8 illustrates the stent retrieval device embodiment of FIG. 1, distal of guide catheter distal end 23. The device is shown in inflated, open position, having larger inside diameter than in the non-pressurized state. As illustrated in FIG. 8, the device distal region is sufficiently large enough to contain stent proximal end 32.

With the aid of radiographic visualization, tube 52 is advanced until tube distal end 90 surrounds stent proximal end 32. Tube 52 is further advanced, guiding stent 30 into the center axis of the tube. With the stent at least partially within tube 64, inflation fluid pressure is removed, causing tube 52 to resume its non-pressurized, smaller profile. This causes ribs 64 to grasp and compress stent 30. With the stent firmly grasped as illustrated in FIG. 9, tube 52 is withdrawn proximally toward the guide catheter distal end. Shoulder 62 is drawn first into the guide catheter, centering tube 52 within the guide catheter and presenting a smooth contour for withdrawal. Tube 52 is further withdrawn, exiting the patient's body and the guide catheter.

In use, the embodiment of FIG. 4, is used in cooperation with an elongate tube such as a guide catheter. Referring to FIG. 6, an embodiment having a cavity such as longitudinal cavity 222, can be side mounted onto balloon catheter shaft 26. Fingers 202 are closed into a configuration similar to that of FIG. 5, and inserted into the guide catheter proximal end. Grasping device 201 is advanced by pushing shaft 212. While advancing, grasping device 201 may have a configuration slightly more open than that illustrated in FIG. 5. Upon exiting guide catheter distal end 23, fingers 202 are opened to the configuration of FIG. 4, opening the grasping device, embodied by web 206 over fingers 202. The device opening can be effected by moving first shaft 212 distally or second shaft 214 proximally. Device 201 is advanced until touching stent 30. At this point, device 201 has an effective inside diameter where stent proximal end 32 touches web 206. Fingers 202 close over stent proximal end 32, thereby decreasing the effective inside diameter of device 201. Finger closing can be effected by sliding first shaft 212 proximally or second shaft 214 distally. Shaft 212 is withdrawn, and, in the preferred method, balloon catheter shaft 26 is also withdrawn, drawing stent 30 into the guide catheter. Stent 30 may then be withdrawn proximally from the guide catheter and patient using the stent retrieval device.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A stent retrieval device comprising:
   an elongate shaft including a distal region;
   a tube having an exterior, a slit therethrough and an inside diameter, said tube operatively attached to said shaft distal region, means for increasing said tube inner diameter; said means for increasing said tube inner diameter includes an inflatable sleeve attached about said tube exterior.

2. A stent retrieval device comprising:
   an elongate shaft having an inflation lumen and a distal region;
   a tube having a slit therethrough and an inside diameter operatively attached to said shaft distal region, said tube having a wall including an inner and outer surface;
   an inflatable sleeve attached about said tube outer surface, said sleeve being in fluid communication with said shaft inflation lumen.

3. A stent retrieval device as recited in claim 2, wherein said slit is a longitudinal slit.

4. A stent retrieval device as recited in claim 3, wherein said tube includes a plurality of reinforcing ribs.

5. A stent retrieval device as recited in claim 4, wherein said tube includes a proximal region and a distal region, said device further comprising a tube proximal shoulder extending proximally from said tube proximal region, decreasing proximally in outer diameter.

6. A method for retrieving a stent comprising:
   providing a stent retrieval device including an elongate shaft having a distal region, a retrieval tube operatively attached to said shaft distal region, said retrieval tube having a slit therethrough and an inflatable sleeve attached about said tube exterior, said retrieval tube increasing in inside diameter when said inflatable sleeve is inflated;
   providing a patient having an elongate tube inserted intravascularly and extending proximally therefrom, having a stent positioned near the distal end of said elongate tube;
   advancing said retrieval tube distally into said patient through said elongate tube;
   advancing the distal end of said retrieval tube until the proximal end of said stent is within proximity of said retrieval tube distal end,
   increasing said retrieval tube inside diameter;
   advancing said retrieval tube over said stent;
   decreasing said retrieval tube inside diameter; and
   retracting said retrieval tube containing said stent proximally.

7. A method as recited in claim 6, wherein said elongate tube is a guide catheter.

8. A method as recited in claim 7, wherein said guide catheter has a balloon catheter inserted therethrough, further comprising selecting a section of the shaft of the balloon catheter proximal to said patient's body and moving said retrieval tube slit over said catheter shaft.

9. A stent retrieval device comprising:
   a first elongate shaft having a longitudinal axis and a distal region;
   a second elongate shaft having a longitudinal axis and a distal region;
   said first and second shaft being slidable relative to one another; and
   a grasping device attached to said first and second shaft distal regions, having an effective inner diameter and a means for reducing said effective inner diameter, said grasping device including a plurality of diverging fingers.

10. A stent retrieval device as recited in claim 9, wherein said fingers include an inner member and an outer member, each having a proximal and distal region,
    said inner and outer members attached to one another distally,
    said inner members operatively attached at said proximal region to said first shaft distal region,
    said outer members operatively attached at said proximal region to said second shaft distal region,
    whereby, pulling said first shaft and pushing said second shaft acts to close said fingers, decreasing the radial extent of said fingers, decreasing the effective inner diameter of said grasping device.

11. A stent retrieval device as recited in claim 10, wherein said second shaft is a tube, having said first shaft lying within.

12. A stent retrieval device as recited in claim 10, wherein said grasping device includes an elastomeric web between said fingers.

13. A stent retrieval device as recited in claim 10, wherein, when said grasping device is open, said inner members diverge radially from said shaft longitudinal axis with increasing distal longitudinal distance, and, when said grasping device is open, said outer members converge radially toward said shaft longitudinal axis with increasing proximal distance.

14. A stent retrieval device as recited in claim 10, wherein said first shaft distal region includes a longitudinal cavity.

15. A stent retrieval device as recited in claim 10, wherein said first shaft distal region includes an attachment hub having a longitudinal cavity.

16. A method for retrieving a stent comprising:

providing a stent retrieval device including a first elongate shaft having a distal region, a second elongate shaft having a distal region, said second shaft being hollow and said first shaft lying within said second shaft, and a grasping device, having a proximal region and a distal region, attached to said first and second shaft distal regions, said grasping device including a plurality of diverging fingers;

providing a patient having an elongate tube inserted intravascularly and extending proximally therefrom, having a stent positioned near the distal end of said elongate tube;

advancing said grasping device distally into said patient through said elongate tube;

advancing said grasping device past the distal end of said elongate tube;

advancing said grasping device over the proximal end of said stent;

closing said grasping device over said stent;

withdrawing said grasping device within said elongate tube; and withdrawing said grasping device containing said stent proximally.

17. A method as recited in claim 16, wherein said elongate tube is a guide catheter.

18. A method as recited in claim 17, wherein the distal region of said grasping device includes a longitudinal slit and said guide catheter has a balloon catheter inserted therethrough, further comprising selecting a section of the shaft of the balloon catheter proximal to said patient's body and mounting said grasping device slit over said catheter shaft.

\* \* \* \* \*